US006852316B2

(12) United States Patent
Vinson et al.

(10) Patent No.: US 6,852,316 B2
(45) Date of Patent: Feb. 8, 2005

(54) CANCER TREATMENT

(75) Inventors: Gavin Paul Vinson, London (GB); John Richard Puddefoot, London (GB); Miles Gordon Berry, London (GB)

(73) Assignee: Queen Mary & Westfield College, London (GB)

( * ) Notice: Subject to any disclaimer, the term of this patent is extended or adjusted under 35 U.S.C. 154(b) by 0 days.

(21) Appl. No.: 09/784,005

(22) Filed: Feb. 16, 2001

(65) Prior Publication Data

US 2002/0119142 A1 Aug. 29, 2002

Related U.S. Application Data

(63) Continuation of application No. PCT/GB99/02727, filed on Aug. 18, 1999.

(30) Foreign Application Priority Data

Aug. 18, 1998 (GB) .............................................. 9818023
Sep. 14, 1998 (GB) .............................................. 9820000

(51) Int. Cl.[7] .............................................. A61K 38/48

(52) U.S. Cl. .................................................. 424/94.63

(58) Field of Search ..................................... 424/94.63

(56) References Cited

FOREIGN PATENT DOCUMENTS

WO  WO 97/34627 A2   9/1997
WO  WO 97/34627 A3   12/1997

OTHER PUBLICATIONS

Takahashi et al., Journal of Japan Surgical Society, Jul. 1991, 92(7), 775–84.*
Iwasaki et al., Japanese Journal of Cancer and Chemotherapy, Sep. 1995, 22(11), 1674–8.*
Yamaue te at al., Arch. Jpn. Chir., 59(4), 302–9, 1990.*
Kitamura et al., Japanese Journal of Cancer and Chemotherapy, 8(2), 1657–60, 1990.*
Ohigashi et al., Hepato–Gastroenterology, 43, 1996, 338–345.*
Carter et al., Br. J. Cancer, 1992, 65, 37–39.*
English Translation of Iwasaki, Y., et al., "Intrahepatic Arterial Infusion Chemotherapy wth Anginotensin II for Liver Metastasis from Gastric Cancer," Jpn. J. Cancer Chemother. 25:1412–1414, Gan To Kagaku Ryohosha (Jul. 1998), Ralph McElroy Translation Company (Document AT3).
English Translation of Tsuji, Y., et al., "One Case of Inoperable Pancreatic Carcinoma With 4 Years Survival by Intra–arterial Infusion with Angiotensin–II Used Concomitantly," Jpn. J. Cancer Chemother. 23:1617–1619, Gan To Kagaku Ryohosha (1996), Ralph McElroy Translation Company (Document AT5).

English Translation of Takahashi, N., "Tissue concentrations of 5–FU and clinical investigation of angiotensin–II concomitant cancer chemotherapy," Journal of Japan Surgical Society 92:775–783, Nippon Geka Gakkai (1991), Ralph McElroy Translation Company (Document U cited in Examiner's PTO–892 form, mailed Jun. 18, 2002).
English Translation of Iwasaki, Y., et al., "A Case of Intrahepatic Infusion Chemotherapy with Human Angiotensin II for Liver Metastasis from Early Gastric Cancer," Japanese J. of Cancer Chemother. 22:1674–1677, Gan to Kagaku Ryohosha (1995), Ralph McElroy Translation Company (Document V cited in Examiner's PTO–892 form, mailed Jun. 18, 2002).
English Translation of Kitamura, M., et al., "Evaluation of Liver and Peritoneal Metastasis Treatment for Gastric Carcinoma Intra–arterial Injection in Terms of Survival Period," Japanese J. of Cancer Chemother. 17:1657–1660, Gan To Kagaku Ryohosha (1990), Ralph McElroy Translation Company (Document X cited in Examiner's PTO–892 form, mailed Jun. 18, 2002).
Gui, G.P.H., et al., "Integrin expression in primary breast cancer and its relation to axillary nodal status," Surgery 117:102–108, Mosby–Year Book, Inc. (1995).
Gui, G.P.H., et a., "Altered cell–matrix contact: a prerequisite for breast cancer metastasis?" Br. J. Cancer 75:623–633, Churchill Livingstone (Sep. 1997).
Hart, I.R. and Saini, A., "Biology of tumor metastasis," Lacet 339:1453–1457,Williams & Wilkins (1992).
Hynes, R.O., "Integrins: Versatility, Modulation, and Signaling in Cell Adhesion," Cell 69:11–25, Cell Press (1992).
Inwang, E.R., et al., "Angiotension II type 1 receptor expression in human breast tissues," Br. J. Cancer 75:1279–1283, Churchill Livingstone (Nov. 1997).
Iwasaki, Y., et al., "Intrahepatic Arterial Infusion Chemotherapy with Angiotensin II for Liver Metastasis from Gastric Cancer," Jap. J. Cancer Chemotherapy 25:1412–1415, Gan to Kagaku Ryohosha (Jul. 1998).
Jeunemaitre, X., et al., "Molecular Basis of Human Hypertension: Role of Angiotensin," Cell 71:169–180, Cell Press (1992).
Peach, M.J., "Renin–Angiotensin System: Biochemistry and Mechanisms of Action," Physiol. Rev. 57:313–370, American Physiological Society (1977).
Pignatelli, M., et al., "Integrins and Their Accessory Adhesion Molecules in Mammary Carcinomas: Loss of Polarization in Poorly Differentiated Tumors," Hum. Pathol. 23:1159–1166, W.B. Saunders Company (1992).

(List continued on next page.)

Primary Examiner—Michael Meller
(74) Attorney, Agent, or Firm—Sterne, Kessler, Goldstein & Fox P.L.L.C.

(57) ABSTRACT

The present invention relates to the use of angiotensin in a method for the treatment or prevention of cancer. The method comprises administering to a patient in need of treatment an effective amount of an angiotensin.

9 Claims, 3 Drawing Sheets

OTHER PUBLICATIONS

Ruoslahti, E. and Pierschbacher, M.D., "New Perspectives in Cell Adhesion: RGD and Integrins," *Science* 238:491–497, American Association for the Advancement of Science (1987).

Tahmasebi, M., et al., "Transcription of the Prorenin Gene in Normal and Diseased Breast," *Eur. J. Cancer* 34:1777–1782, Elsevier Science Ltd. (Oct. 1998).

Tsuji, Y., et al , "A Case of Non–resectable Pancreatic Cancer Suriving More Than 4 Years by Intra–arterial Infusion Chemotherapy with Angiotensin–II," *Jap. J. Cancer Chemotherapy* 23:1617–1620, Gan To Kagaku Ryohosha (1996).

Vinson, G.P., et al , "The distribution of angiotensin II type 1 receptors, and the tissue renin–angiotensin systems," *Mol. Med. Today* 1:35–39, Elsevier Science Ltd. (1995).

Yamada, K.M., et al , "Monoclonal Antibody and Synthetic Peptide Inhibitors of Human Tumor Cell Migration," *Cancer Res.* 50:4485–4496, American Association for Cancer Research (1990).

Zhang, Z., et al , "The $\alpha\beta 1$ Integrin Functions As a Fibronectin Receptor But Does Not Support Fibronectin Matrix Assembly and Cell Migration on Fibronectin," *J. Cell Biol.* 122:235–242, Rockefeller University Press (1993).

Zutter, M.M., et al., "Decreased Expression of Integrin Adhesive Protein Receptors in Adenocarcinoma of the Breast," *Am. J. Pathol.* 137:863–870, American Society of Pathology (1990).

Albelda, S.M. and Buck, C.A., "Integrins and other cell adhesion molecules," *FASEB J.* 4:2868–2880, Federation of American Societies of Experimental Biology (1990).

Berry, M.G., et al., "Angiotensin II Upregulates Intergrin $\beta 1$ Expression in Human Breast Cancer Cells," *Mol. Biol. Cell.* 9(suppl):418A, Abstract No. 2424, American Society for Cell Biology (Nov. 1998).

Ferrario, C.M., "The Renin–Angiotensin System: Importance in Physiology and Pathology," *J. Cardiovasc. Pharmacol 15 Suppl.* 3:s1–s5, Raven Press, Ltd. (1990).

* cited by examiner

A II-PRETREATED; ANTI-β1+ve

A II-PRETREATED; ANTI-β1-ve

A II UNTREATED; ANTI-β1+ve

A II UNTREATED; ANTI-β1-ve

CANCER TREATMENT

The present application is a continuation of the international application. PCT/GB99/02727, filed Aug. 18, 1999, and published in English as WO 00/10590 on Mar. 2, 2000. which claims priority benefit to Great Britain applications GB 9818023.5, filed Aug. 18, 1998 and GB 9820000.9, filed Sep. 14, 1998. The full disclosures of each of these applications is herein incorporated by reference.

The present invention relates to the use of angiotensin in a method for the treatment or prevention of cancer.

The renin-angiotensin system (RAS) is the name given to the system of substrates and enzymes that gives rise to the active circulating hormone, angiotensin-II. Renin is a proteolytic enzyme secreted into the bloodstream by the juxtaglomerula cells of the kidney. It cleaves a substrate, angiotensinogen, which is a component of the $\alpha_2$-globulin fraction of the plasma proteins to yield a decapeptide called angiotensin-I. Two amino acids from the carboxyl terminus of this peptide are, in turn, cleaved by angiotensin converting enzyme (ACE) to produce the active octapeptide angiotensin II:

Asp-Arg-Val-Tyr-Ile-His-Pro-Phe (SEQ ID NO:1).

Other enzymes may act on angiotensin-I or -II to yield angiotensin-III (des-Asp$^1$-angiotensin-II) or angiotensin 1-7, but is generally thought that angiotensin-II has the greatest biological significance (Vinson et al *Mol. Medicine Today* 1 35–38 (1995)). Using in situ hybridisation methods, it has been shown that the prorenin gene is actively transcribed in fibroblasts surrounding the breast ducts in normal tissue. This arrangement becomes distorted in the cancerous breast, in which prorenin gene transcription becomes attenuated, and may cease altogether (Tahmasebi et al *Eur. J. Cancer*—in press (1998)).

Historically, angiotensin-II has been recognised for its central role in mammalian electrolyte homeostasis and haemodynamics (Peach, M. T., *Physiol. Rev.* 57 313–370 (1977)), particularly through the regulation of aldosterone secretion and cardiovascular function. At a pathological level, the RAS has a significant role in hypertension: ACE antagonists are a valuable tool in the treatment of this disease (Ferrario, C. M., *J. Cardiovasc. Pharmacol.* 15 (Suppl. 3) S1–S5 (1990)). The genes encoding both ACE and angiotensin are considered to be candidates contributing to the pathogenesis of hypertension and cardiovascular disease (Jeunemaitre et al *Cell* 71 169–180 (1992)).

Angiotensin exerts is biological effects via specific receptors of which there are two main subtypes classified as $AT_1$ and $AT_2$. Most of the known physiological functions of angiotensin-II appear to be mediated via the $AT_1$ receptor, but the widespread incidence of the $AT_2$ receptor suggests that it has specific roles (Vinson et al *Mol. Medicine Today* 1 35–38 (1995)). The $AT_1$ receptor is widely distributed in many tissue types and appears to be particularly abundant in epithelial tissue. The $AT_1$ receptor has also found to be present at a higher than normal density in breast cancer epithelial cells leading to the suggestion that $AT_1$ receptors may have a functional bearing on the development of breast cancer (Vinson et al *Mol. Medicine Today* 1 35–38 (1995)), or that angiotensin may be involved in the development of cancer (Vinson et al *B. J. Cancer* 75 (9) 1279–1283 (1997)).

As a cause of mortality, cancer is second only to cardiovascular disease. The commonest sites of cancer in populations in Europe or North America are lung, skin, large bowel, prostate, stomach, rectum in men, and breast, large bowel, skin, lung and cervix in women. The overall mortality rates may, though, be different from the incidence rates. Cancer incidence also shows a variation geographically with certain countries or areas having rates of incidence for certain types of cancer. To date, many factors have been identified as being responsible for the development of cancer and these include: chemical carcinogens, irradiation (ionising radiation and UV radiation, including sunlight), viruses and genetic factors. Cancer cells that proliferate in the body but stay together form benign tumours; those that not only proliferate but also shed cells, e.g. via the blood or lymphatic system (metastasis) to form colonies elsewhere form malignant tumours.

Metastasis is a remarkable process and one which is still poorly understood. The risk of metastases increases as tumours become larger. The cells must survive tissue invasion, circulation, passage across the capillary wall, and establishment in tissues. The process of tissue penetration appears to be by secretion of enzymes known as metalloproteinases (such as collagenase). The precise location of a metastasis is probably due in part to chance. However, clinical patterns of blood-borne metastasis have been observed. For example, gut cancers spread through the portal venous system to the liver; ovarian cancers seed into the peritoneal space; breast cancer has a tendency to spread to the bones of the axial skeleton; and sarcomas often spread into the lung (Souhami, R. L. and Moxham, J., *Textbook of Medicine*, Second edition, Churchill Livingstone, New York (1994)). A long term goal in the treatment of cancer is the prevention of the spread of the primary tumour by metastasis and the development of secondary tumours elsewhere in the body.

A key feature of metastasis is a disruption of the normal regulation of the integrin class of cell adhesion molecules. The integrins are members of a large family of cell adhesion molecules which include the cadherins, selectins and immunoglobulins. The integrins are receptors that normally modulate cell-matrix as well as cell-cell adhesion and play an important part in a diverse range of biological processes including organogenesis, growth and inflammation by influencing cell migration, anchorage and differentiation (Albelda, S. M. and Buck, C. A., *FASEB J.* 4 2868–2880 (1990)). A disturbance in the normal control of integrin function predisposes to pathological conditions, including tumour invasion and metastasis (Hart, I. R. and Saini, A., *Lancet* 329 1453–1461 (1992)). During tumour progression, cell adhesion activity is involved in altered (i) cell—cell and (ii) cell-substratum attachment, and (iii) cell migration and invasion through basement membranes, thereby releasing tumour cells into the circulation or lymphatic system. These three processes are probably mediated by different receptors (Zhang et al *J. Cell Biol.* 122 235–242 (1993)). Each process thus forms a different step of the metastatic cascade and a combination of all three is likely to be required for metastasis to occur. The various cell adhesion molecule families probably act in conjunction since current evidence cannot attribute this complicated process to a single sub-group.

Integrins are transmembrane receptors, each one being a glycoprotein heterodimer consisting of varying $\alpha$- and $\beta$-subunits. Fourteen $\alpha$- and eight $\beta$-subunits have been described and these associate to form 20 known integrins (Hynes, R. O. *Cell* 69 11–25 (1992)). The integrins recognise a variety of important basement membrane and matrix proteins including laminin, collagen, fibronectin and vitronectin (Ruoslahti, E. and Pierschbacher, M. D., *Science* 238 491–497 (1987); Yamada et al *Cancer Res.* 50 4485–4496 (1990)).

In glandular epithelium, the principle integrins are members of the $\beta_1$, $\beta_2$, $\beta_3$, $\beta_4$ and $\beta_5$ subfamilies and selective loss of their expression in primary breast cancer cells has been described (Koukoulis et al *Am. J. Pathol.* 137 863–870 (1990); Pignatelli et al *Hum. Pathol.* 23 1159–1166 (1992); Gui et al *Surgery* 117 102–108 (1995)). In addition, a significant relationship has been shown between loss of specific integrin expression on primary breast cancer cells and the presence of axillary nodal metastasis (Gui et al *Surgery* 117 102–108 (1995)). More importantly, using malignant epithelial cells taken directly from these patients, it has been discovered that both the specific integrin loss and lymph node invasion are related to reduced adhesive properties of those cells derived from patients with nodal metastasis (Gui et al *British J. Cancer* 117 623–633 (1996)).

It has now been surprisingly discovered that angiotensin induces integrin production in cancer cells in contrast to its previously supposed role and that as a result angiotensin can inhibit cancer cell invasiveness.

According to first aspect of the present invention there is provided a method of treatment or prevention of metastasis of cancer cells comprising the step of administering to a patient in need of treatment an effective amount of an angiotensin. This aspect of the invention also extends to the use of an angiotensin in the preparation of a medicament for the prevention or treatment of metastasis of cancer cells.

The present invention therefore offers a significant advance in the treatment of cancer which should permit the early and effective treatment of aggressive malignant tumours in preventing or inhibiting the spread from the primary tumour location. Angiotensin is a naturally occurring biologically active molecule which should be tolerated well by the body in contrast to existing chemotherapeutic agent or radiotherapy currently used to treat cancer.

In the present invention, the angiotensin molecule may be angiotensin-II, although it is envisaged that alternative synthetic forms of the hormone could be made by substitution of one or more amino acids in the molecule. The invention therefore extends to the use of a molecule having angiotensin activity. The skilled person is aware that various amino acids have similar properties. One or more such amino acids of a substance can often be substituted by one or more other such amino acids without eliminating a desired activity of that substance. Thus the amino acids glycine, alanine, valine, leucine and isoleucine can often be substituted for one another (amino acids having aliphatic side chains). Of these possible substitutions it is preferred that glycine and alanine are used to substitute for one another (since they have relatively short side chains) and that valine, leucine and isoleucine are used to substitute for one another (since they have larger aliphatic side chains which are hydrophobic). Other amino acids which can often be substituted for one another include: phenylalanine, tyrosine and tryptophan (amino acids having aromatic side chains); lysine, arginine and histidine (amino acids having basic side chains); aspartate and glutamate (amino acids having acidic side chains); asparagine and glutamine (amino acids having amide side chains); and cysteine and methionine (amino acids having sulphur containing side chains). Substitutions of this nature are often referred to as "conservative" or "semi-conservative" amino acid substitutions.

Amino acid deletions or insertions may also be made relative to the amino acid sequence of angiotensin. Thus, for example, amino acids which do not have a substantial effect on the activity of angiotensin, or at least which do not eliminate such activity, may be deleted. Amino acid insertions relative to the sequence of angiotensin can also be made. This may be done to alter the properties of a substance of the present invention (e.g. to assist in identification, purification or expression, where the protein is obtained from a recombinant source, including a fusion protein. Such amino acid changes relative to the sequence of angiotensin from a recombinant source can be made using any suitable technique e.g. by using site-directed mutagenesis. The angiotensin molecule may, of course, be prepared by standard chemical synthetic techniques, e.g. solid phase peptide synthesis, or by available biochemical techniques, e.g. enzymatic treatment of angiotensinogen with renin.

It should be appreciated that amino acid substitutions or insertions within the scope of the present invention can be made using naturally occurring or non-naturally occurring amino acids. Whether or not natural or synthetic amino acids are used, it is preferred that only L-amino acids are present.

Whatever amino acid changes are made (whether by means of substitution, insertion or deletion), preferred polypeptides of the present invention have at least 50% sequence identity with a polypeptide as defined in a) above more preferably the degree of sequence identity is at least 75 %. Sequence identities of at least 90% or at least 95% are most preferred.

The degree of amino acid sequence identity can be calculated using a program such as "bestfit" (Smith and Waterman, Advances in Applied Mathematics, 482–489 (1981)) to find the best segment of similarity between any two sequences. The alignment is based on maximising the score achieved using a matrix of amino acid similarities, such as that described by Schwarz and Dayhof (1979) Atlas of Protein Sequence and Structure, Dayhof, M. O., Ed pp 353–358. Where high degrees of sequence identity are present there will be relatively few differences in amino acid sequence.

Metastasis of cancer cells is the process by which cancer cells from a malignant primary tumour invade the surrounding tissue and spread out into the body to seed secondary tumours. Secondary tumours are also capable of undergoing metastasis to spread further. Metastasis can also be characterised as the invasiveness potential of a cancer tumour. A method or use in accordance with this aspect of the invention can therefore be used to reduce and/or inhibit the invasiveness potential of a cancer cell.

The present invention will be generally applicable to all forms of cancer, but it is to breast cancer that the invention should find particular utility. Other cancers which may be treated include, but are not limited to, skin cancer (melanoma), large bowel cancer, prostate cancer, lung cancer, bone cancer, or cancer of the cervix, stomach, or rectum.

A medicament comprising an angiotensin may be prepared by standard pharmaceutical techniques known in the art depending upon the mode of administration and the particular disease to be treated. The medicament will usually be supplied as part of a sterile, pharmaceutical composition which will normally include a pharmaceutically acceptable carrier. This pharmaceutical composition may be in any suitable form, (depending upon the desired method of administering it to a patient). It may be provided in unit dosage form, will generally be provided in a sealed container and may be provided as part of a kit. Such a kit would normally (although not necessarily) include instructions for use. It may include a plurality of said unit dosage forms.

The pharmaceutical composition may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Such compositions may be prepared by any method known in the art of pharmacy, for example by admixing the active ingredient with the carrier(s) or excipient(s) under sterile conditions.

Pharmaceutical compositions adapted for oral administration may be presented as discrete units such as capsules or tablets; as powders or granules; as solutions, syrups or suspensions (in aqueous or non-aqueous liquids; or as edible foams or whips; or as emulsions). Suitable excipients for tablets or hard gelatine capsules include lactose, maize starch or derivatives thereof, stearic acid or salts thereof. Suitable excipients for use with soft gelatine capsules include for example vegetable oils, waxes, fats, semi-solid, or liquid polyols etc. For the preparation of solutions and syrups, excipients which may be used include for example water, polyols and sugars. For the preparation of suspensions oils (e.g. vegetable oils) may be used to provide oil-in-water or water in oil suspensions. In certain situations, delayed release preparations may be advantageous and compositions which can deliver an angiotensin in a delayed or controlled release manner may also be prepared. Prolonged gastric residence brings with it the problem of degradation by the enzymes present in the stomach and so enteric-coated capsules may also be prepared by standard techniques in the art where the angiotensin is for release lower down in the gastro-intestinal tract.

Pharmaceutical compositions adapted for transdermal administration may be presented as discrete patches intended to remain in intimate contact with the epidermis of the recipient for a prolonged period of time. For example, the active ingredient may be delivered from the patch by iontophoresis as generally described in *Pharmaceutical Research,* 3(6):318 (1986).

Pharmaceutical compositions adapted for topical administration may be formulated as ointments, creams, suspensions, lotions, powders, solutions, pastes, gels, sprays, aerosols or oils. For infections of the eye or other external tissues, for example mouth and skin, the compositions are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base. Pharmaceutical compositions adapted for topical administration to the eye include eye drops wherein the active ingredient is dissolved or suspended in a suitable carrier, especially an aqueous solvent. Pharmaceutical compositions adapted for topical administration in the mouth include lozenges, pastilles and mouth washes.

Pharmaceutical compositions adapted for rectal administration may be presented as suppositories or enemas.

Pharmaceutical compositions adapted for nasal administration wherein the carrier is a solid include a coarse powder having a particle size for example in the range 20 to 500 microns which is administered in the manner in which snuff is taken, i.e. by rapid inhalation through the nasal passage from a container of the powder held close up to the nose. Suitable compositions wherein the carrier is a liquid, for administration as a nasal spray or as nasal drops, include aqueous or oil solutions of the active ingredient.

Pharmaceutical compositions adapted for administration by inhalation include fine particle dusts or mists which may be generated by means of various types of metered dose pressurised aerosols, nebulizers or insufflators.

Pharmaceutical compositions adapted for vaginal administration may be presented as pessaries, tampons, creams, gels, pastes, foams or spray formulations.

Pharmaceutical compositions adapted for parenteral administration include aqueous and non-aqueous sterile injection solution which may contain anti-oxidants, buffers, bacteriostats and solutes which render the formulation substantially isotonic with the blood of the intended recipient; and aqueous and non-aqueous sterile suspensions which may include suspending agents and thickening agents. Excipients which may be used for injectable solutions include water, alcohols, polyols, glycerine and vegetable oils, for example. The compositions may be presented in unit-dose or multi-dose containers, for example sealed ampoules and vials, and may be stored in a freeze-dried (lyophilized) condition requiring only the addition of the sterile liquid carried, for example water for injections, immediately prior to use. Extemporaneous injection solutions and suspensions may be prepared from sterile powders, granules and tablets. The pharmaceutical compositions may contain preserving agents, solubilising agents, stabilising agents, wetting agents, emulsifiers, sweeteners, colourants, odourants, salts (substances of the present invention may themselves be provided in the form of a pharmaceutically acceptable salt), buffers, coating agents or antioxidants. They may also contain therapeutically active agents in addition to the substance of the present invention.

Dosages of the substance of the present invention can vary between wide limits, depending upon the disease or disorder to be treated, the age and condition of the individual to be treated, etc. and a physician will ultimately determine appropriate dosages to be used.

Without wishing to be bound by theory, it is believed that the angiotensin molecule is promoting cell adhesion by inducing the expression of integrin production in cancer cells. An increase in cell adhesion being mediated by integrin molecules thus leading to a reduced chance for metastasis of cancer cells from a tumour.

According to a second aspect of the present invention there is provided a method of inducing expression of $\beta_1$ integrin molecules in cancer cells comprising the step of administering to a patient an effective amount of an angiotensin. This aspect of the invention also extends to the use of an angiotensin in the preparation of a medicament for the induction of expression of $\beta_1$ integrin molecules in cancer cells.

As described above, the integrin molecules form part of a larger superfamily of related cell adhesion molecules. The $\beta_1$ integrin subunit is found in combination with various $\alpha$-subunits as follows: $\beta_1\alpha_1$ (ligands include collage type-I, -IV, -VI, laminin P1 and E1); $\beta_1\alpha_2$ (ligands include collagen type-I, -IV, laminin, fibronectin); $\beta_1\alpha_3$ (ligands include fibronectin, collagen type-I, laminin (E3), epiligrin; $\beta_1\alpha_4$ (ligands include fibronectin, VCAM-1); $\beta_1\alpha_5$ (ligands include fibronectin); $\beta_1\alpha_6$ (ligands include laminin (E8)); $\beta_1\alpha_7$ (ligands include laminin (E8)); and $\beta_1\alpha_8$ (ligands include fibronectin).

A method or use in accordance with this aspect of the present invention has the advantage of promoting the expression of integrin molecules on cancer cells which can reduce or inhibit the invasiveness potential of the cancer cells. In other words, the promotion of expression of integrin expression can prevent or treat metastasis of cancer cells.

Preferred features for the second and subsequent aspects of the invention are as for the first aspect *mutatis mutandis.*

The present invention will now be described with reference to the following examples and drawings which are present for the purposes of illustration and are not to be construed as being limiting on the invention. In the examples reference is made to a number of drawings, in which.

MATERIALS AND METHODS DETAILS FOR THE EXAMPLES

1. Routine Culture of the MCF-7 Cell Line

1.1 Sources of Cells and Monoclonal Antibodies

MCF-7 cells were obtained from the European Collection of Animal Cell Cultures (ECACC) (Porton Down, Salisbury, Wiltshire). Monoclonal antibodies used were as follows: Anti-$\beta_1$ integrin, MAB1977 (Chemicon, Harrow, Middlesex), Anti-$AT_1R$, 6313/G2 (our own).

1.2. Cell Resuscitation from Routine Storage

Suspensions containing 1 ml MCF-7 cells were removed from frozen storage in liquid nitrogen. The freezing vial was then rapidly defrosted by immersion in a water bath pre-warmed to 37° C. and 5 ml basic culture medium added. Basic culture medium (BCM) for routine culture work comprised minimum essential medium Eagle (MEM) supplemented as in Table 1. The mixture was centrifuged at 900 rpm for 10 minutes to wash the cells and remove potentially toxic dimethyl sulphoxide (DMSO) used in the storage mixture. The cell pellet was resuspended in 5 ml BCM with 20% foetal bovine serum (FBS) and transferred to a 75 cm$^3$ culture flask. The flask was incubated at 37° C. in a 5% $CO_2$-enriched atmosphere until cell growth was established when the content of FBS was reduced to 5%. When the cells had become sub-confluent they could be harvested for use in the in vitro assays.

1.3. Routine Propagation of Cell Lines

Colonies of MCF-7 cells were grown in sterile, 75 cm$^3$ vented-cap culture flasks containing BCM. Incubation was performed in a clean, sterile, humidified, 5% $CO_2$—supplemented environment at a constant temperature of 37° C. Medium was removed and replaced with fresh basic culture medium every 2–3 days and cells were used for functional studies when sub-confluent.

TABLE 1

Supplements added to MEM as basic culture medium

| Supplement | Concentration |
| --- | --- |
| Amphotericin B | 5 U/ml |
| Foetal bovine serum | 5% |
| Gentamicin | 20 μg/l |
| Glucose | 4.5 g/l |
| L-glutamine | 4 mM |
| Non-essential amino acids | 10 ml/l |
| Penicillin | 100 U/ml |
| Sodium pyruvate | 2 mM |
| Streptomycin | 100 μg/ml |

1.4. Recovery of Cells for Routine Subculture and in vitro Studies

Cells were harvested enzymatically with trypsin (0.05% w/v) in EDTA solution (0.02%). Firstly, the effete medium was withdrawn by pipette and the cells washed with phosphate-buffered saline (PBS) (0.15 M sodium chloride, 0.01 M sodium monophosphate, pH 7.5). This was removed and 5 ml trypsin/EDTA added to each flask which was placed into the incubator for 1–2 minutes. The trypsin was removed and the flask replaced in the incubator for a further 2–5 minutes until the cells were either free-floating or could be detached from the flask by gentle tapping. BCM was added and cell pellet recovered by centrifugation (900 rpm, 10 minutes). For routine subculture the pellet was resuspended in 5 ml fresh BCM with 1 ml being added to each of five fresh culture flasks containing 9 ml BCM. For in vitro assays the cell pellet was suspended in serum-free medium to avoid the potential influence of FBS on receptor expression or affinity.

1.5. Replenishment of Cell Stores by Freezing

In order to maintain stocks of MCF-7 cells those superfluous to experimental requirements were frozen down as follows. Sub-confluent cells harvested by trypsinisation were pelleted by centrifugation. Each pellet from a single culture flask was taken up in 5 ml BCM containing 20% FBS to which was added 0.5 ml and DMSO drop-wise with agitation. The mixture was pipetted repeatedly and 1 ml aliquots added to freezing vials which were stored overnight at the top of a liquid nitrogen storage tank. These were then immersed in liquid nitrogen for indefinite storage at −70° C.

2. Immunocytochemistry

Immunocytochemical straining of both receptors was based on the standard streptavidinbiotin peroxidase method. For the optimal working concentration of both antibodies serial dilutions were performed. The $AT_1R$ antibody 6313/G2 in the range 1:1 to 1:500 and for anti-$\beta_1$ integrin between 1:10 and 1:500. It was found that 1:100 and 1:400 respectively yielded the best results.

2.1. Preparation of MCF-7 Cells for Immunocytochemistry

For $AT_1R$ straining, a drop of harvested MCF-7 cells in BCM suspension was placed on Polylysine coated microscope slides (British Drug House, Poole, Dorset) and allowed to air-dry. The slides were immersed in liquid nitrogen and dry-stored in slide-mailers at −80° C. until use. This step appeared to enhance the morphological preservation of the cells.

For integrin $B_1$ receptor straining both with and without A-II pre-treatment, harvested cells were plated onto sterile microscope slides within slide culture wells (Heraeus Instruments GmbH, Osterode am Harz, Germany) and incubated with fresh BCM. When sub-confluent the medium was replaced with serum-free BCM to which was added Angiotensin-II (A-II), or not in the case of controls which were subjected to otherwise identical preparation and straining. Angiotensin-II (A-II) was added in the concentration range $10^{-5}$M to $10^{-9}$M and incubated for 24 hours. The medium was then removed, the slides rinsed with PBS, air dried and stored frozen as above.

2.2. Immunocytochemistry Methodology

The slides, prepared as above, were removed from frozen storage and placed directly into 100% acetone (British Drug Houses) at −10° C. for 10 minutes. They were then air-dried for 10 minutes and rehydrated in 0.05 M Tris-buffered saline (TBS)(0.05 M sodium chloride, 0.05 M Trizma base, 36 mM hydrochloric acid, pH 7.6) twice for 3 minutes each. Endogenous peroxidase was blocked with a 3% solution of hydrogen peroxide (British Drug Houses) in 99.8% methanol (British Drug Houses) for 15 minutes followed by a wash in running tap water for 10 minutes. The slides were then rinsed in TBS three times for 3 minutes. The slides were dried and ringed with hydrophobic marker (Dako Ltd, High Wycombe, Buckinghamshire) prior to the application of normal rabbit serum (Dako) at a dilution of 1:5 in TBS for 20 minutes.

Normal rabbit serum was poured away and the primary antibody applied at the relevant dilution. Incubation in the humidity cabinet for one hour at room temperature was followed by a wash in TBS for five minutes.

The secondary layer, biotinylated rabbit anti-mouse antibody (Dako), at a dilution of 1:400 in TBS, was applied and allowed to incubate as above for 30 minutes.

A five minute wash in TBS preceded the addition of the tertiary layer, streptavidin-biotin-peroxidase conjugate (Dako). This was prepared at least thirty minutes prior to use and the slides were incubated for thirty minutes.

For colour development, the substrate diaminobenzidine tetrahydrochloride solution (DAB) was made fresh immediately prior to use by the addition of one tablet of hydrogen peroxide tablet and one of DAB per 1 ml distilled water. The resultant solution was passed through a 2 μm filter, protected from light exposure and added to the specimens for 10 minutes. The slides were then washed in running water for 10 minutes and counterstained with Harris' haematoxylin for two minutes. A further wash in running preceded dehydration through graded alcohol immersion (70%, 85% and 100%) for 3 minutes each. Two five minute soaks in xylene (British Drug House) completed the procedure and the strained sections were mounted with Distrene 80 dibutylphthalate xylene (DPX) (British Drug House).

Each experiment was performed a minimum of three time and control sections were incubated in the absence of primary antibody with TBS and culture medium for MAB 1977 and 6313/G2 respectively.

3. Immunoprecipitation of $\beta_1$ Integrin

The method used is based upon those of Gullberg et al *J. Biol. Chem* 264 12686–12694 (1989) and Burgess et al *Circ. Res.* 74 291–298 (1994).

Immunoprecipitation is a technique for the detection and quantification of target protein. It comprises the five steps of radiolabelling of the cell-membrane proteins, cell lysis, formation of the specific antibody-antigen complexes, extraction of these complexes and analysis of the radiolabelled target proteins contained within the immunoprecipitation. All experiments were performed in triplicate.

3.1. Preparation of Cells for Immunoprecipitation

For immunoprecipitation experiments, MCF-7 cells were cultured in 5% FBS-supplemented MEM. When subconfluent, the medium was removed and the cells washed with phosphate buffered saline (PBS) (0.15 M sodium chloride, 20 mM sodium monophosphate; pH 7.5). The medium was then replaced with serum-free MEM and treated with angiotensin-II (A-II) at a concentration of $10^{-5}$ M for 24 hours. Control cells were cultured in serum-free medium only. On this occasion the cells were harvested not by trypsinisation, which may impair the immunoprecipitation process, but with a cell scraper. They were then gently passed repeatedly through a narrow pipette, to break down cell clusters, and centrifuged at 900 rpm per ten minutes.

3.2. Radio-Labelling of Cell Surface Proteins

The cell pellets as above were taken up in PBS and counted with the haemocytometer. Trypan blue exclusion was employed so that 1–2×10$^6$ viable cells were taken up in each 1 ml aliquot. To each cell suspension was added 1 mCi of $^{125}$I (Amersham International PLC, Little Chalfont, Bucks.) and five IODO-BEADS (Pierce & Warriner (UK) Ltd, Chester). The latter comprises N-chlorobenzenesulfonamide (sodium salt) immobilised on non-porous, uniform, polystyrene beads which induce protein iodination through oxidation. The beads were washed with PBS and dried on filter paper prior to use as their efficacy can be adversely effected by moisture. The reaction was allowed to proceed at room temperature and stopped after 20 minutes by removal of the IODO-BEADS with forceps.

3.3. Lysis of the Cell Preparations

This, the critical step in immunoprecipitation, aims to solubilise all target protein in a form which is immunoreactive and not degraded. Extraction of membrane-bound proteins, such as integrin $\beta_1$, requires a mixture of ionic and non-ionic detergents to counteract the effect of intracellular enzymes, released as a consequence of cell lysis, which may digest the target protein. For this reason conditions detrimental to proteolysis are maintained. These include maintaining the cell extracts on ice (4° C.) at all times and including protease inhibitors in the lysis/solubilisation buffer. Table 2 lists the protease inhibitors used in this method.

TABLE 2

Properties of protease inhibitors used in immunoprecipitation

| Inhibitor | Activity |
|---|---|
| Aprotinin | Trypsin |
|  | Chymotrypsin |
|  | Plasma |
|  | Kallikrein |
| Leupeptin | Trypsin |
|  | Plasmin |
|  | Papain |
|  | Cathepsin B |
| Pepstatin A | Pepsin |
|  | Cathepsin D |
| Phenlymethyl-sulphonylfluoride | Trypsin |
|  | Chymotrypsin |

The radio-iodinated cells were washed three times with 500 μl cold PBS and incubated on a vertical rotator for 30 minutes with 100 μl of solubilisation buffer (1 mmol/l calcium chloride, 1 mmol/l magnesium chloride, 10 mmol/l Tris-HCl and 1% Triton X-100; pH 8) containing protease inhibitor cocktail (1% aprotinin, 1 μg/ml benzamidine, 2 mmol/l leupeptin, 1 μg/ml pepstatinA, 1 mmol/l phenylmethyl sulphonyl fluoride). The samples were the centrifuged at 15,000 g for 30 minutes and 1 μl of the supernatant was sampled to confirm, and calculate the degree of, incorporation of $^{125}$I into solubilised membrane proteins prior to immunoprecipitation.

3.4. Immunoprecipitation of Target Protein

In order to immunoprecipitate the target protein, monoclonal antibody was added to the cell lysates and the secondary antibody-protein complexes formed were collected by absorption onto protein A-Sepharose beads. This step allows for very little non-specific absorption of non-target proteins to the protein A/Sepharose beads. Background, produced by non-specific absorption of non-target proteins, was minimised by prior incubation of the lysate in an end-over-end fashion with 1 μl of rat immunoglobulins (Dako Ltd, High Wycombe, Buckinghamshire) for four hours.

10 μl of a 50% slurry of protein A/Sepharose 4B in PBS was added for one hour. The mixture was centrifuged at 10,000 g for 10 minutes and 100 μg/ml anti-$\beta_1$ integrin antibody (mab13, Becton Dickinson, Oxford, Oxfordshire) added to the supernatant. Following overnight incubation a further 10 μl of protein A/Sepharose 4B slurry was added for one hour.

The tertiary protein A/Sepharose 4B-antibody complexes were collected by centrifugation at 10,000 g for five minutes. These were then washed to displace proteins non-specifically absorbed to the protein A/Sepharose 4B five times with buffer 1 (1 mmol/l manganese chloride, 500 mmol/l Sodium chloride, 10 mmol/l Tris-HCl, 1% Triton X-100; pH 7.4), three times with buffer 2 (0.5% deoxycholate, 1 mmol/l manganese chloride, 100 mmol/l sodium chloride, 10 mmol/l Tris-HCl, 1% Triton X-100; pH 7.6) and trice with PBS. 100 μl of sodium dodecylsulphate (SDS) loading buffer (Bio-rad Laboratories Ltd, Hemel Hempsted, Hertfordshire) loading buffer was added to the final pellet and the mixture was boiled for 5 minutes to denature and detach the proteins from the Sepharose beads. A final centrifugation at 12,000 g for 20 seconds allowed the protein contained within the supernatant to be separated from the protein A/Sepharose 4B beads.

4. Sodium Dodecylsulphate-polyacrylamide Gel Electrophoresis (SDS-PAGE) of Immunoprecipitated Proteins Proteins are analysed by electrophoresis in polyacrylamide gels under conditions that ensure dissociation into component polypeptide subunits with minimal aggregation. The detergent SDS, in combination with boiling, dissociates the proteins before they are loaded onto the gel. The strongly anionic SDS binds the denatured polypeptides which themselves become negatively charged. The amount of SDS bound is proportional to the molecular weight of the polypeptide irrespective of the sequence and thus distance that the SDS-polypeptide complexes migrate through the gel is inversely proportional to the molecular weight. The concomitant running of marker proteins with known molecular weights allows confirmation of the molecular weight of the sample. The SDS-polypeptide complexes migrate in response to an electric current.

The samples (15 μl) are first loaded into wells created in the stacking buffer. This is highly porous and allows concentration of the sample in a very thin zone at the surface of the running gel: this has the effect of increasing the resolution.

Polyacrylarnide gels comprise polymerised and cross-linked acrylaride chains. Bisacrylamide cross-links not only add rigidity and tensile strength, but also create pores through which sample complexes pass. Large molecular weight proteins such as the integrin $\beta_1$ subunit (115,000 non-reducing, 105,000 reducing) are optionally resolved using an acrylamide concentration of 7.5%.

4.1. Preparation of SDS-PAGE Apparatus

Two glass plates were thoroughly washed in distilled water and wiped with 100% alcohol, taking care not to leave fingerprints on the glass. Spacers were inserted between the sides of the plates which were clamped, placed into the stand and locked in position. Distilled water was run between the plates to ascertain watertightness then drained away. Running gel (7.2 ml acrylamide/bisacrylamide, 300 μl ammonium persulphate, 15 ml distilled water, 7.5 ml running buffer, 300 μl 10% SDS solution, 20 μl $N,N,N^1,N^1$-tetramethylethylenediamine (TEDED)) was instilled between the glass plates without delay because TEMED rapidly polymerises the gel. It was filled to 2 cm below the silicon comb and a layer of water gently run onto the gel both to smooth the surface and exclude air bubbles: the oxygen in these bubbles can diffuse into the gel an inhibit polymerisation. The apparatus was left to stand at room temperature for 45–60 minutes until setting occurred.

The water was poured away and stacking gel (1.37 ml acrylamide/bisacrylamide, 50 μl ammonium persulphate, 6 ml distilled water, 2.5 ml stacking buffer (0.5 M Tris-HCl; pH 6.8), 100 μl 10% SDS solution, 10 μl TEMED) added with the comb in situ to form the sample wells. The gel was left for a further 15–30 minutes and, when fully set, was removed from the casting stand and placed in the tank. This was filled with electrode buffer (200 mM glycine, 3 mM sodium dodecylsulphate, 25 mM Trizma-base), ensuring coverage of the upper electrode.

4.2. Running the SDS-PAGE Gel

Equal quantities of the treated and control untreated samples were then carefully installed into individual wells using a glass syringe. Known molecular weight protein markers were added to a separate well and the apparatus connection to the power supply. The gel was run at a voltage of 200V over 3–5 hours until the bromophenol dye, contained with the SDS loading buffer, had reached the bottom of the running gel.

4.3. Gel Analysis by Autoradiography

When it had finished running the power was disconnected and the glass plates were separated. The gel was wrapped in cling film and, in a dark room, placed adjacent to photographic film (BioMax Light-1) thus allowing the emitted γ radiation to produce an image of the $^{125}$I-labelled integrin $\beta_1$, proteins within the gel. The ensemble was placed into a film cassette and stored at −80° C. for 2 to 4 days. Once the film had been adequately exposed it was developed automatically.

EXAMPLES 1 to 4

Example 1

Figure 1:
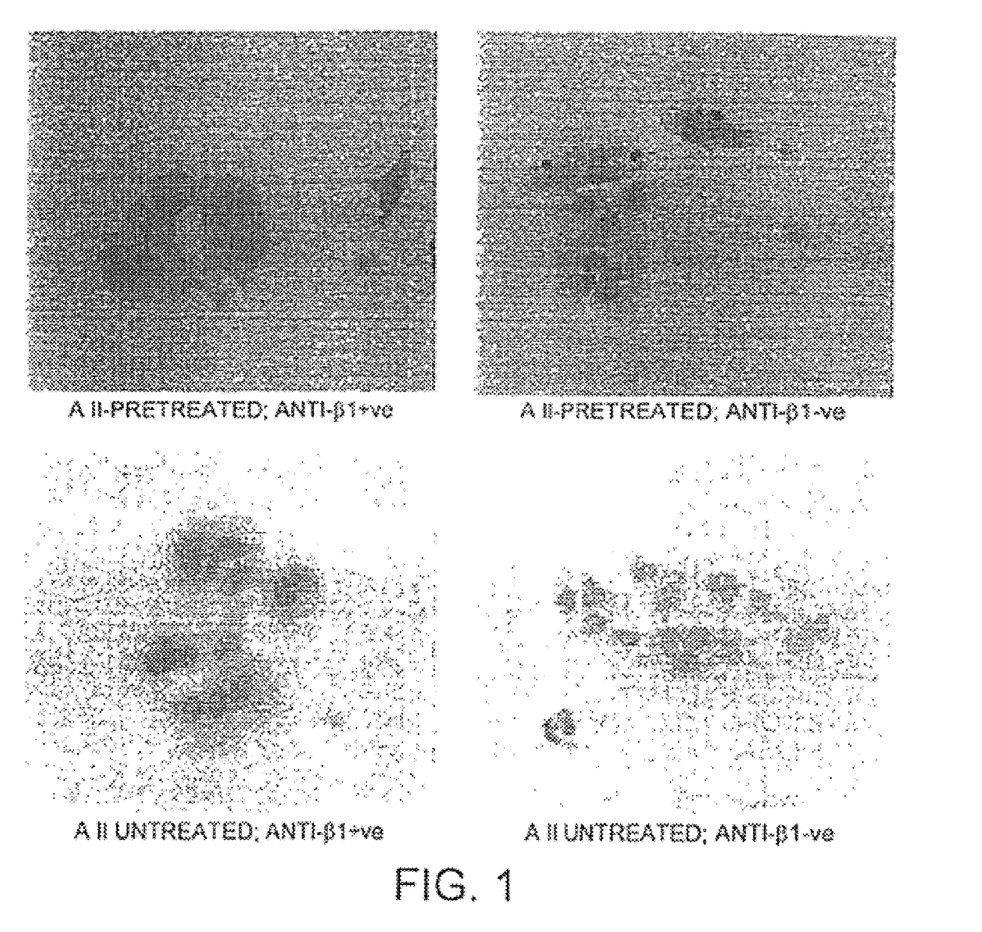
FIG. 1 shows images of MCF-7 cancer cell line preparations having undergone immunocytochemistry for the $\beta_1$ integrin subtype (×40 magnification).

Immunocytochemical Study of Effect of Angiotensin-II on $\beta_1$ Integrin Expression in MCF-7 Cancer Cell Line The effect of Angiotensin-II on $\beta_1$ integrin expression in MCF-7 subtype cancer cell line was studied using immunocytochemistry and the results are shown in FIG. 1. The evident increase in staining of cells treated with angiotensin-II (A-II) at $10^{-5}$ M demonstrates the increase expression of $\beta_1$ integrin protein.

Example 2

Labelling of $\beta_1$ Integrin Protein with $I^{125}$

Figure 2:
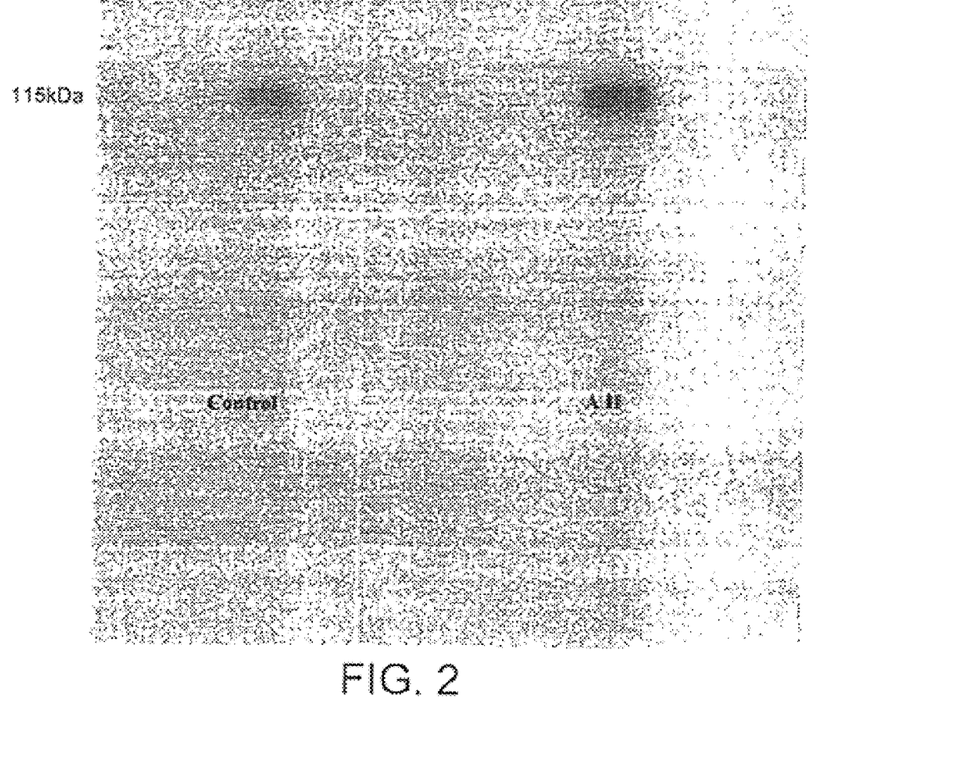
FIG. 2 shows a digitised image of a gel autoradiograph demonstrating relative increase in density of angiotensin-II (A-II) pre-treated protein band compared to control under non-reducing conditions.

Cell surface proteins were labelled with $I^{125}$ to study expression of the $\beta_1$ integrin subtype. After labelling, the $\beta_1$ integrin was immunoprecipitated with an anti-$\beta_1$ integrin antibody. FIG. 2 shows the result of an autoradiograph demonstrating the increased expression of $\beta_1$ integrin after treatment with angiotensin-II (A-II) compared to a control sample.

Example 3

Effect of Angiotensin-II on Breast Cell Cancer Invasion

Figure 3:
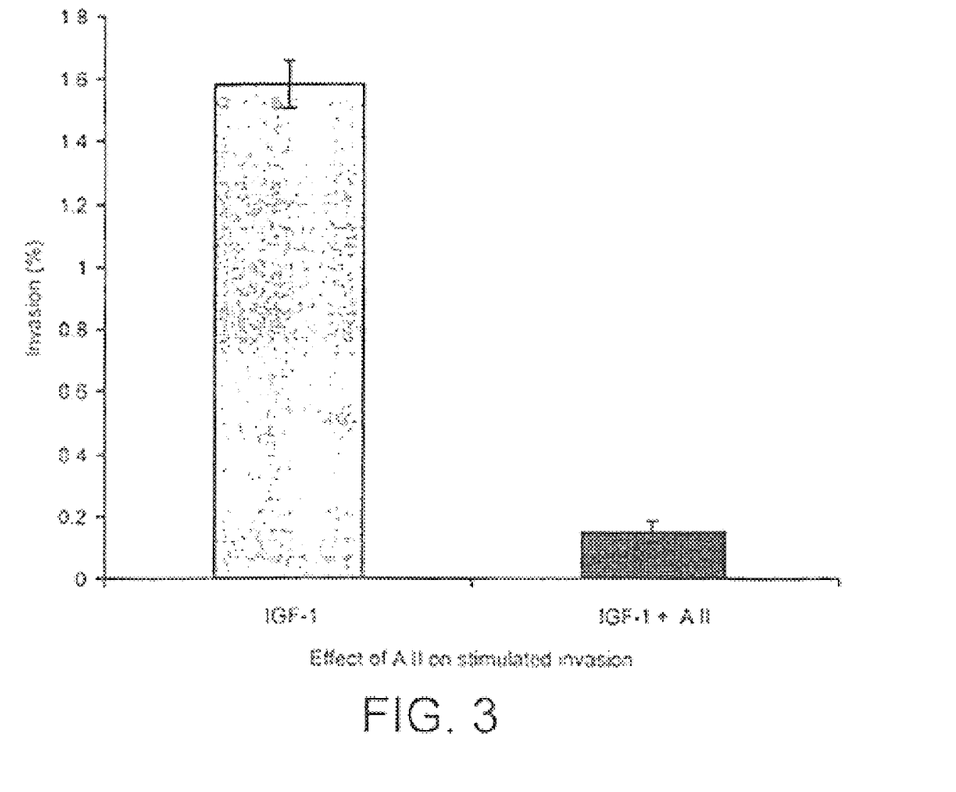
FIG. 3 shows a graph of the effect of angiotensin-II on breast cancer cell invasion in which inhibition of IGF-I stimulated invasion after pre-treatment with angiotensin-II (A-II) is compared to a control without A-II treatment.

The effect of angiotensin-II (A-II) in inhibiting growth factor-induced stimulated cancer cell invasiveness was studied as a model system and the results are shown in FIG. 3. The study was carried out using an invasion chamber in which two compartments are separated by a perforated membrane coated in matrix protein. A chemoattractant, IGF-I, was added to the medium on one side of the chamber, and the breast cancer cells to the other. Invasiveness was measured by counting the cells that migrated from one chamber to the other. Treating the cells with angiotensin-II (A-II) prior to the invasion assay led to a tenfold reduction in mean invasion from 1.58% to 0.15% (p=0.0011). The invasiveness potential of the cancer cells was therefore markedly inhibited by angiotensin-II.

Example 4

Studies of Effect of Angiotensin-II on Breast Cancer Cell Growth in Culture

It was observed by light microscopy that breast cancer cells grown in culture in the presence of angiotensin-II, tended to produce larger clusters of cells than cells grown in control cultures. At the same time, angiotensin-II did not stimulate cell growth suggesting that it had a role in cell-cell adgesion and cell migration.

What is claimed is:

1. A method of treatment of metastasis of cancer cells consisting of administering to a patient in need thereof an effective amount of a composition consisting essentially of angiotensin-II.

2. The method as claimed in claim 1, wherein said cancer cells are selected from the group consisting of breast, skin, large bowel, prostate, lung, bone, cervix, stomach and rectum.

3. The method as claimed in claim 1, wherein said administering is oral, rectal, nasal, topical, vaginal, or parenteral.

4. The method as claimed in claim 1, wherein said administering is subcutaneous, intramuscular, intravenous, or intradermal.

5. The method as claimed in claim 1, wherein said composition further comprises an excipient or carrier.

6. A method of treatment of metastasis of cancer cells comprising administering to a patient in need thereof an effective amount of a composition consisting essentially of angiotensin-II, wherein said cancer cells are selected from the group consisting of skin, prostate, bone and cervix.

7. The method as claimed in claim 6, wherein said composition further comprises an excipient or carrier.

8. The method as claimed in claim 6, wherein said administering is oral, rectal, nasal, topical, vaginal, or parenteral.

9. The method as claimed in claim 6, wherein said administering is subcutaneous, intramuscular, intravenous, or intradermal.

* * * * *

SEQUENCE LISTING

<160> NUMBER OF SEQ ID NOS: 1

<210> SEQ ID NO 1
<211> LENGTH: 8
<212> TYPE: PRT
<213> ORGANISM: Unknown
<220> FEATURE:
<223> OTHER INFORMATION: Sequence Source Uncertain

<400> SEQUENCE: 1

Asp Arg Val Tyr Ile His Pro Phe
1               5